US008430872B2

(12) United States Patent
Mardirossian et al.

(10) Patent No.: US 8,430,872 B2
(45) Date of Patent: Apr. 30, 2013

(54) SYSTEMS AND/OR METHODS FOR USING COHERENT ELECTROMAGNETIC WAVES TO TREAT TUMORS AND/OR OTHER GROWTHS

(75) Inventors: Aris Mardirossian, Potomac, MD (US); William Fourney, Laurel, MD (US)

(73) Assignee: Avogadro, Maxwell, Boltzman, LLC, Potomac, MD (US)

( * ) Notice: Subject to any disclaimer, the term of this patent is extended or adjusted under 35 U.S.C. 154(b) by 688 days.

(21) Appl. No.: 12/659,036

(22) Filed: Feb. 23, 2010

(65) Prior Publication Data

US 2011/0208176 A1    Aug. 25, 2011

(51) Int. Cl.
*A61B 18/18*    (2006.01)

(52) U.S. Cl.
USPC ............................................................ 606/33

(58) Field of Classification Search ............... 606/32–48
See application file for complete search history.

(56) References Cited

U.S. PATENT DOCUMENTS

| | | | | |
|---|---|---|---|---|
| 4,643,514 A | * | 2/1987 | Raviv et al. | 600/108 |
| 5,203,782 A | * | 4/1993 | Gudov et al. | 606/31 |
| 5,261,404 A | * | 11/1993 | Mick et al. | 600/425 |
| 5,384,573 A | * | 1/1995 | Turpin | 342/179 |

OTHER PUBLICATIONS

Outwater, et al., "A Guide to Practical Holography," http://www.holo.com/holo//book/book.html, 1995-2004.

* cited by examiner

*Primary Examiner* — Michael Peffley
*Assistant Examiner* — Amanda Scott
(74) *Attorney, Agent, or Firm* — Nixon & Vanderhye P.C.

(57) ABSTRACT

Certain example embodiments relate to techniques for using coherent electromagnetic (EM) waves to treat tumors and/or other growths. In certain example embodiments, a growth is imaged. Based on this image, a holographic plate is prepared. Coherent electromagnetic waves are then focused on the holographic plate so that a holographic image of the growth is formed on the actual growth. Magnetic particles may be injected at or proximate to the growth and captured in the EM field corresponding to the holographic image such that these injected particles are caused to congregate in and/or on the growth. In certain example embodiments, bombarding of the growth with the injected particles may help damage or destroy the tumor. In certain example embodiments, the particles, once attached to and/or embedded in the actual growth may be irradiated (e.g., using a microwave or other energy source) so as to further damage or destroy the growth.

20 Claims, 5 Drawing Sheets

SYSTEMS AND/OR METHODS FOR USING COHERENT ELECTROMAGNETIC WAVES TO TREAT TUMORS AND/OR OTHER GROWTHS

FIELD OF THE INVENTION

Certain example embodiments of this invention relate to systems and/or methods for treating tumors and/or other growths. More particularly, certain example embodiments of this invention relate to systems and/or methods for using coherent electromagnetic (EM) waves to treat tumors and/or other growths. In certain example embodiments, a holographic EM field is created on an imaged tumor or other growth to cause injected particles to congregate in and/or on the tumor or other growth, and the particles are irradiated to damage or destroy the tumor or other growth.

BACKGROUND AND SUMMARY OF EXAMPLE EMBODIMENTS OF THE INVENTION

Since the discovery of holography in 1947, holograms have gained notoriety through science fiction television shows and movies. For instance, holograms were popularized through the "holodeck" in the Star Trek television and movie franchise. Today, holograms are widely recognizable in security-type applications such as, for example, logos on credit/debit cards or "officially licensed" goods, imprints on certain bank notes or bills (including certain Euro, Japanese Yen, British Pound, Canadian Dollar, and/or other bank notes or bills), in "identigrams" (such as those used in Germany), and/or the like. Another recent avenue of exploration involves the use of holograms for data storage applications.

In holography, some of the light scattered from an object (or set of objects) is made to fall on a recording medium. This first set of light is often referred to as the "object beam." A second light beam, often referred to as the "reference beam," also illuminates the recording medium such that the object and reference beams interfere with one another. The resulting light field, which appears to be a random pattern of varying intensity, is the hologram. It the hologram is illuminated by the original reference beam (or suitable substitute reference beam, e.g., with the same wavelength, curvature, and angle), a light field is diffracted by the reference beam that is identical to the light field that was scattered by the object (or objects). Thus, someone looking into the hologram "sees" the objects even though it may no longer be present.

In a typical recording process used for a complex object, a laser beam is split into two separate beams of light using a beamsplitter (e.g., typically half-silvered glass or a birefringent material). One beam (the object beam) illuminates the object, reflecting the object's image onto the recording medium as it scatters the beam, and the second beam (the reference beam) illuminates the recording medium directly. According to diffraction theory, each point in the object acts as a point source of light. Each of these point sources interferes with the reference beam, giving rise to an interference pattern. The resulting pattern is the sum of the point source and reference beam interference patterns.

In a typical reproduction process used in connection with transmission-type holograms, the holographic plate is illuminated by the reference beam (or a suitable substitute, as described above). When this happens, each point source diffraction grating will diffract part of the reference beam to reconstruct the wavefront from its point source, and these individual wavefronts add together to reconstruct the whole of the object beam. In so doing, a viewer will be able to perceive a wavefront that is identical to the scattered wavefront of the object illuminated by the reference beam such that the viewer sees an image (or holographic projection) of the original object. This image is sometimes known as a "virtual image." The direction of the light source seen illuminating the virtual image is that of the original illuminating beam. As indicated above, to reconstruct the object exactly from a transmission hologram, the reference beam must have the same wavelength and curvature, and must illuminate the hologram at the same angle as the original reference beam (i.e., only the phase can be changed). If these conditions are not met, then the virtual image will appear as a distorted version of the original object. Other types of holograms, such as reflection holograms, also are known.

Although holography techniques have been in place for some years, the inventor of the instant application has realized that holograms have potential uses in fields beyond those described above. In this regard, the inventor of the instant application has realized that holograms that work with non-optical beams have potential uses in the medical field (e.g., beyond the use of holography techniques used in x-ray holography, endoscopic holography, and/or the like). More particularly, the inventor of the instant application has realized that one area where non-optical beam holography may be especially advantageous is in the medical field in connection with the treatment of tumors and/or other growths.

Thus, one aspect of certain example embodiments of this invention pertains to techniques for using coherent electromagnetic (EM) wave related holography to treat tumors and/or other growths. More particularly, in certain example embodiments, a holographic EM field is created on a pre-imaged tumor or other growth to cause injected particles to congregate in and/or on the tumor or other growth, and the particles are irradiated to damage or destroy the tumor or other growth.

In certain example embodiments of this invention, a method of treating a patient having a growth is provided. Characteristics of the growth are determined via an imaging system. A hologram corresponding to the growth is generated using the determined characteristics. A holographic image is projected on the growth, with the holographic image being projected in connection with a substantially coherent electromagnetic wave source. Magnetic particles are injected into the patient. The magnetic particles are caused to migrate towards the projected holographic image so as to become attached to and/or embedded in the growth.

In certain example embodiments of this invention, a system for treating a patient having a growth is provided. An imaging system is configured to determine characteristics of the growth. A controller is configured to generate a hologram corresponding to the growth, with the hologram being generated in dependence on said determined characteristics. A holographic projection system is configured to project a holographic image on the growth, with the holographic image being projected in connection with a substantially coherent electromagnetic wave source. The holographic projection system is further configured to generate a magnetic field in and/or on the growth such that magnetic particles injected into the patient will become attached to and/or embedded in the growth.

In certain example embodiments of this invention, a method of treating a patient having a growth is provided. Characteristics of the growth are determined via an imaging system. A hologram corresponding to the growth is generated using the determined characteristics. The characteristics of the growth include the size, shape, and/or placement of the growth. A holographic image is projected on the growth, with the holographic image being projected in connection with a substantially coherent electromagnetic wave source. Particles are injected into the patient. The particles are caused to migrate towards the projected holographic image so as to become attached to and/or embedded in the growth. The particles are irradiated with microwaves so as to at least partially damage and/or destroy the growth.

According to certain example embodiments, the determining step is repeated for the growth after the growth has been at least partially damaged to determine characteristics of the at least partially damaged growth. A new holographic image is re-projected on the at least partially damaged growth. The magnetic particles are again caused to migrate towards the projected holographic image so as to become attached to and/or embedded in the at least partially damaged growth. The particles are once again irradiated with microwaves so as to further damage and/or destroy the growth.

The features, aspects, advantages, and example embodiments described herein may be combined to realize yet further embodiments.

BRIEF DESCRIPTION OF THE DRAWINGS

These and other features and advantages may be better and more completely understood by reference to the following detailed description of exemplary illustrative embodiments in conjunction with the drawings, of which.

DETAILED DESCRIPTION OF EXAMPLE EMBODIMENTS OF THE INVENTION

Certain example embodiments of this invention relate to systems and/or methods for using coherent electromagnetic (EM) waves to treat tumors and/or other growths. In certain example embodiments, a tumor or other growth is imaged. Based on this image, a holographic plate is prepared such that a holographic projection of the tumor or other growth may be generated therefrom. Electromagnetic waves are then focused on the holographic plate as a reference beam so that a holographic image of the tumor or other growth is formed on the actual tumor or other growth. Magnetic particles may be injected at or proximate to the tumor or other growth and may be captured in the EM field corresponding to the holographic image such that these injected particles are caused to congregate in and/or on the tumor or other growth. In certain example embodiments, the bombarding of the tumor or other growth with the injected particles may help damage or destroy the tumor. In certain example embodiments, the particles, once attached to and/or embedded in the actual tumor or other growth may be irradiated (e.g., using a microwave or other energy source) so as to further damage or destroy the tumor or other growth.

Figure 1:
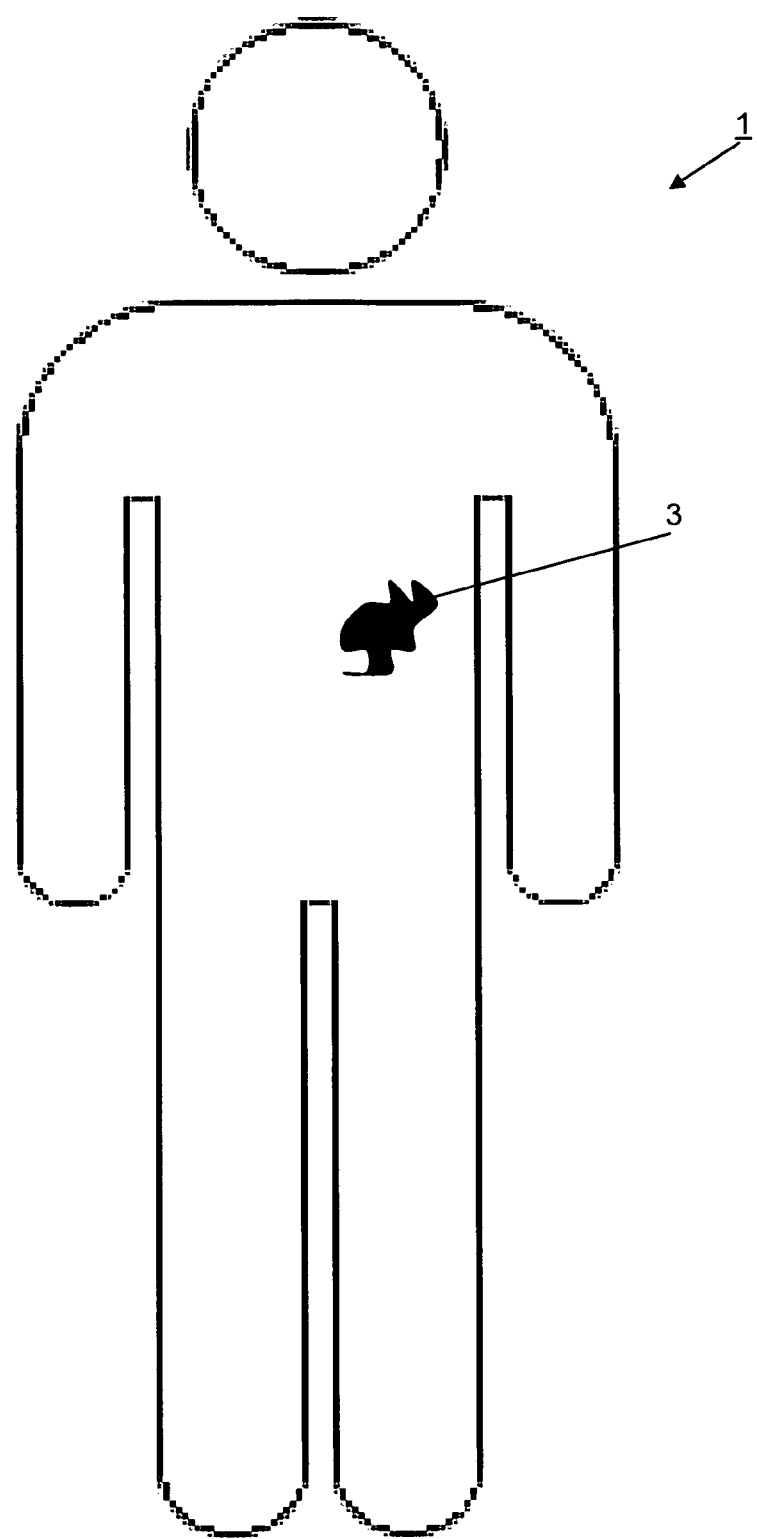
FIG. 1 is a stylized view of a potentially deleterious growth in a human patient.

The removal of tumors, cancerous, and/or other potentially dangerous growths oftentimes present medical challenges, particularly when they are located in difficult to access areas of the body. Although it is possible to surgically remove some growths, others cannot be readily removed. A common approach to treating some forms of cancer involves chemotherapy. Chemotherapy involves a "shotgun-like" approach, whereby a physician "aims" at a general area. This approach, however, is oftentimes harmful, as it affects other regions of the body. FIG. 1 is a stylized view of a potentially deleterious growth 3 in a human patient 1. The growth 3 is provided proximate to the lungs of the patient 1, and thus may be difficult to remove with common surgical techniques. As will be appreciated from the below, certain example embodiments of this invention provide "rifle-shots" directed at the growth 3 to help damage and/or destroy it completely. In other words, certain example embodiments target the growth 3 directly and reduce the potential impact to other parts of the body.

Figure 2:
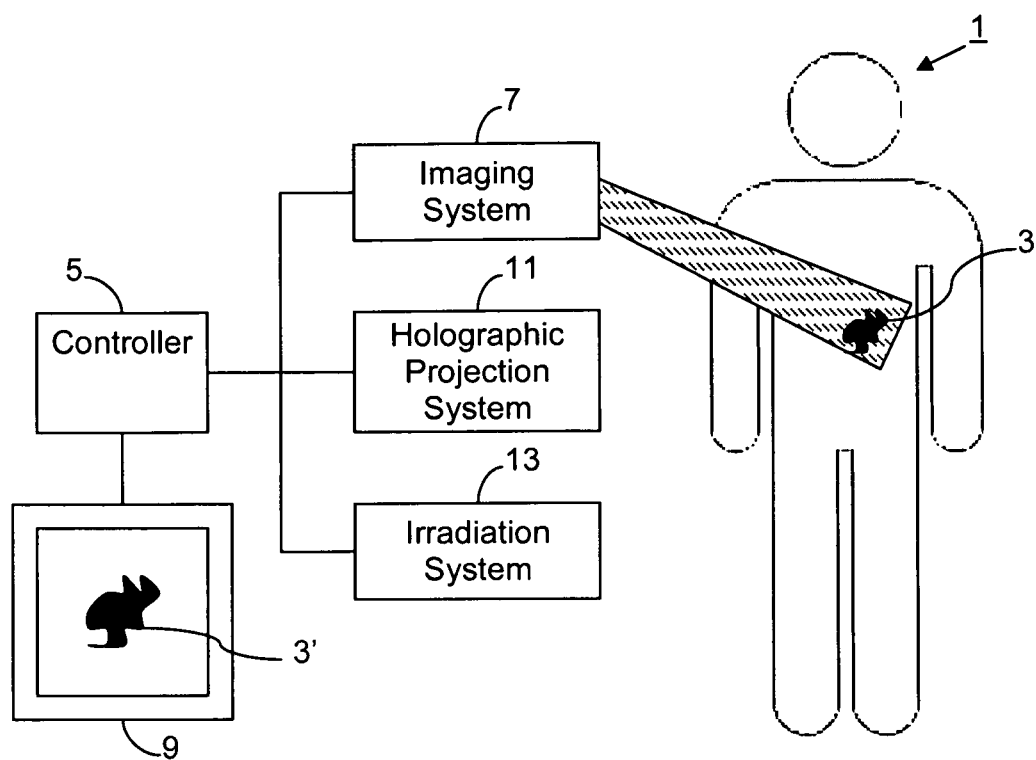
FIG. 2 is a schematic view of an illustrative system imaging the potentially deleterious growth in accordance with an example embodiment.

FIGS. 2-5 help demonstrate principles of the holographic techniques for use with the systems/methods of certain example embodiments. FIG. 2 is a schematic view of an illustrative system imaging the potentially deleterious growth 3 in accordance with an example embodiment. Although not shown in FIG. 2, the patient 1 may be placed on a special table that is designed to keep the patient as still as possible. Such a table may include springs and/or other mechanisms to absorb shocks, vibrations, movements caused by breathing, and/or the like, in certain example instances. The patient may be sedated to help aid with the imaging techniques described in connection with FIG. 2.

In any event, the system includes a controller 5, which coordinates with an imaging system 7, a display 9, a holographic projection system 11, and an irradiation system 13. In FIG. 2, the controller 5 causes the imaging system 7 to obtain a precise view of the growth 3. This view may be digitized and outputted as an image 3' on the display 9. The imaging system 7 itself may be any appropriate imaging apparatus that is capable of obtaining a high-resolution image (including, for example, size, shape, relative and/or absolute position and/or orientation, etc.) of the growth 3. In certain example embodiments, the imaging system 7 may comprise a known CT (computed tomography), CAT (computed axial tomography), MRI (magnetic resonance imaging), ultrasound, and/or other suitable scanner. Even holographic techniques (such as x-ray holography, endoscopic holography, and/or the like) may be used for imaging purposes in certain example embodiments. In certain example embodiments, combinations or sub-combinations of these and/or other imaging systems may be implemented to obtain an accurate view and dimensional description of the growth 3.

As alluded to above, the imaging system 7 may help determine precise characteristics of the growth 3. This information may include, for example, size, shape, relative and/or absolute position and/or orientation, etc. The controller 5 (which may include a processor, a memory, a computer readable storage medium, and/or the like) may take the information from the imaging system 7 and develop a holographic plate corresponding to the growth 3. The development of a holographic plate is possible because all (or substantially all) of the interactions between the object and reference beams, as well as the shapes of the interference fringes, can be modeled using known mathematical equations. Given this model, it is possible to print a suitable pattern onto a holographic plate, thereby indirectly creating a hologram.

Figure 3:
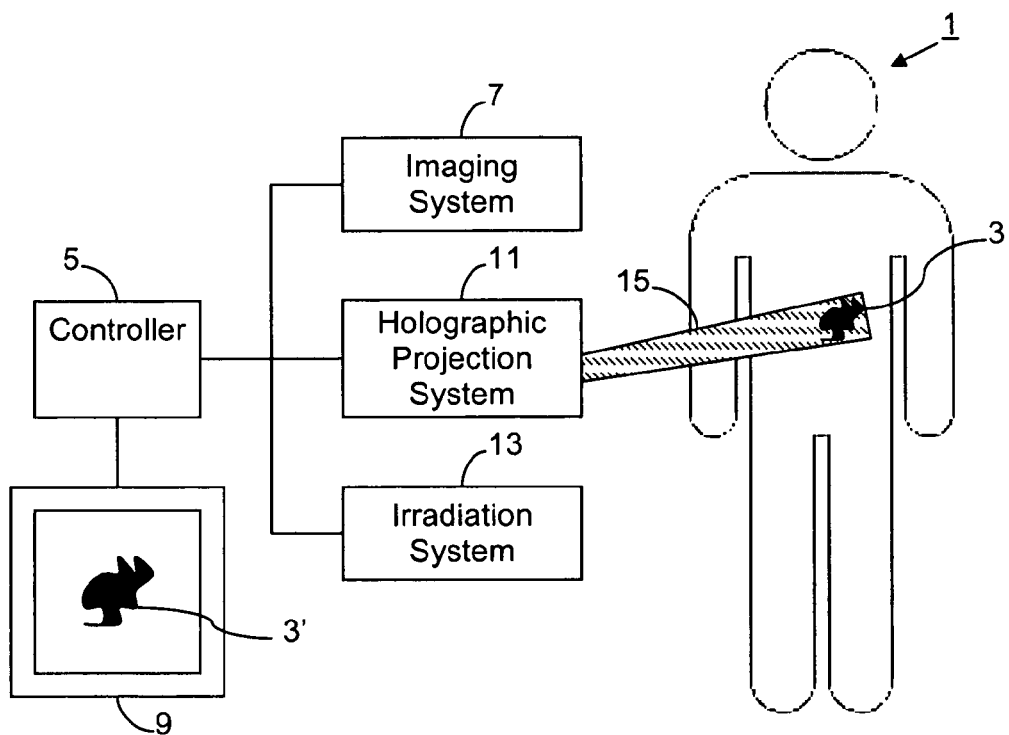
FIG. 3 is a schematic view of the illustrative system of FIG. 2 projecting a holographic image on the potentially deleterious growth in accordance with an example embodiment.

FIG. 3 is a schematic view of the illustrative system of FIG. 2 projecting a holographic image on the potentially deleterious growth in accordance with an example embodiment. Using the holographic plate prepared above, the holographic projection system 11 may superimpose a holographic image on the growth 3. This may be accomplished through the use of a substantially coherent electromagnetic (EM) wave source in conjunction with the holographic plate. It will be appreciated that the substantially coherent electromagnetic (EM) wave source will produce substantially in-phase energy that has substantially the same wavelength. In other words, substantially coherent EM radiation 15 will combine with the holographic plate to produce a magnetic field image of the growth 3. In certain example embodiments, shielding may be provided to absorb and/or protect other portions of the patient's body from the EM radiation 15. For instance, lead and/or other shields may be provided around the area of the patient's body that is to be irradiated.

Magnetic particles may be injected into the patient 1, e.g., at or proximate to the growth 3. Such particles may be coated in Teflon or formed from a material such that the chance of the material oxidizing is reduce. The particles may be of any suitable size and/or shape. In certain example embodiments, for instance, the particles may be substantially spherical and may have a diameter of about 3-7 microns, e.g., so as to match or be just smaller than the size of the white blood cells. In certain example embodiments, the particles may have a width or diameter of less than about 10 microns.

The magnetic field corresponding to the holographic image may cause the particles to migrate towards the growth 3. In particular, the EM field corresponding to the holographic image may help cause these injected particles to congregate in and/or on the tumor or other growth. In certain example embodiments, the bombarding of the tumor or other growth with the injected particles may help damage or destroy the tumor. It will be appreciated that the strength of the magnetic field will be sufficient to particle migration in certain example embodiments. In certain example embodiments, however, the strength of the magnetic field will be insufficient to cause migration of the iron in the patient's blood stream. This may be accomplished by varying the strength of the magnetic field created and/or adjusting the magnetic permeability of the particles (e.g., through appropriate material selection, preparation, and/or the like).

Figure 4:
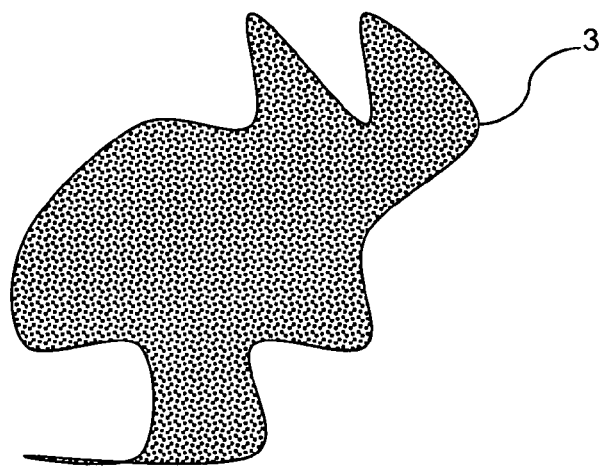
FIG. 4 is an enlarged, stylized view of particles congregating in and/or on the potentially deleterious growth in accordance with an example embodiment.

FIG. 4 is an enlarged, stylized view of particles congregating in and/or on the potentially deleterious growth in accordance with an example embodiment. In certain example embodiments, the EM field corresponding to the holographic image may help cause the particles to attack only the outer surface(s) of the growth 3. In such cases, the controller 5 may coordinate with the holographic projection system 11 to scale down the holographic images such that smaller and smaller images are successively formed, thereby causing the particles to iteratively work away at and/or otherwise break apart the outer surface(s) of the growth 3, e.g., so that it continues to shrink as it is further and further damaged. Because the growth 3 may be dense, certain example embodiments may briefly terminate the holographic projection system 11 and/or create an alternate image slightly larger than the growth 3 so that the particles will initially drift or be forced away from the growth so that they can be subsequently accelerated towards the growth 3 and thus impact it with a greater force. In a similar fashion, the holographic image may in certain example embodiments be made smaller than the growth 3 so that the particles are made to burrow into the growth 3.

Although not explicitly shown in FIG. 4, the imaging system 7 and the holographic projection system 11 may work in tandem or in concert so that substantially continuous, periodic, and/or on-demand information is provided on the display 9.

Figure 5:
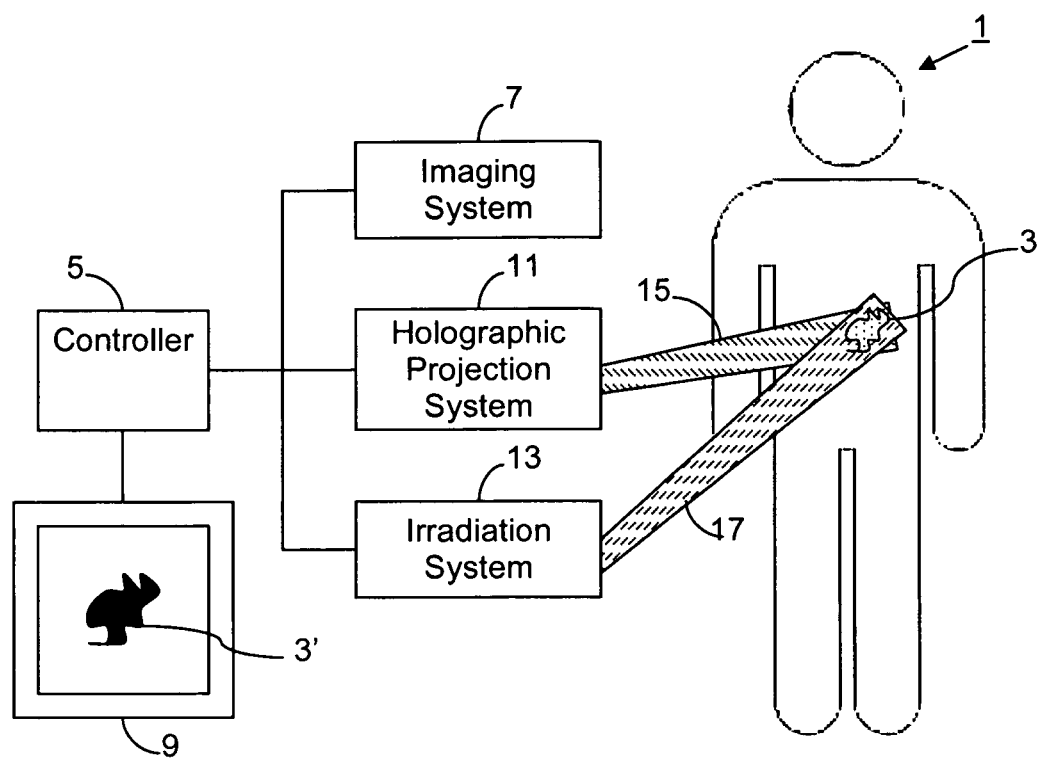
FIG. 5 is a schematic view of the illustrative system of FIG. 2 irradiating the particles that have congregating in and/or on the potentially deleterious growth in accordance with an example embodiment.

FIG. 5 is a schematic view of the illustrative system of FIG. 2 irradiating the particles that have congregating in and/or on the potentially deleterious growth in accordance with an example embodiment. In FIG. 5, the holographic projection system 11 is activated so as to form the holographic image. The irradiation system 13 then emits energy 17 towards the growth 3. For instance, microwave radiation may be focused on the growth 3, e.g., using the coordinate and/or other information obtained by the imaging system 7 and under the control of the controller 5. The irradiation system 13 may help damage and/or destroy the growth 3, e.g., by heating and/or otherwise affecting the particles attached thereto and/or embedded therein. In certain example instances, the particles may be preferentially heated and/or reacted, e.g., by varying their size, composition, positioning, etc.

Compaction techniques similar to the above also may be used in connection with certain example embodiments, e.g., so that irradiation system 13 affects more and more of the growth 3. Also similar to the above, although not explicitly shown in FIG. 5, the imaging system 7, the holographic projection system 11, and/or the irradiation system 13 may work in tandem or in concert so that substantially continuous, periodic, and/or on-demand information is provided on the display 9, and/or so that the above-described and/or similar compaction and bombarding techniques (e.g., by repeatedly removing or otherwise expanding the holographic image so that the particles separate from the tumor and then causing the particles to accelerate towards the tumor, thereby impacting it with a greater force) may be used in connection with certain example embodiments.

Figure 6:
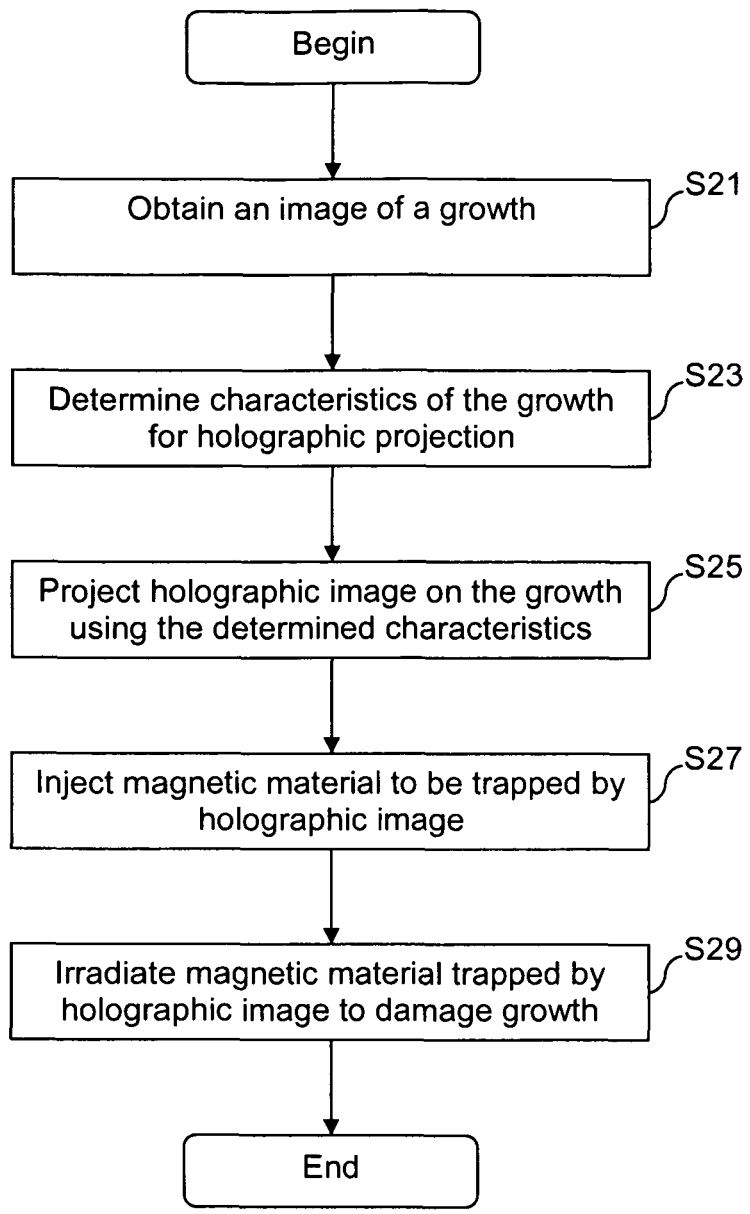
FIG. 6 is a flowchart showing an illustrative process for treating a tumor or other growth in accordance with an example embodiment.

FIG. 6 is a flowchart showing an illustrative process for treating a tumor or other growth in accordance with an example embodiment. An image of a growth (e.g., a tumor, cancerous growth, etc.) is obtained in step S21. From this image, in step S23, characteristics of the growth are determined. Such characteristics may include, for example, size and shape of the growth, position and/or orientation of the growth (e.g., in absolute terms or relatively, for instance, as coordinates within a patient's body, etc.), and/or the like. In step S25, a holographic image may be projected on the growth using the determined characteristics. The holographic image may be formed using coherent electromagnetic (EM) waves, such that the field becomes a magnetic field. In step S27, magnetic material to be trapped by the holographic image superimposed on the growth may be injected into the patient's body. The magnetic material trapped by the holographic image may be irradiated in step S29, thereby damaging and/or destroying the growth.

This technique may be repeated in whole or in part, e.g., so as to damage and/or destroy the growth in pieces in certain example embodiments. This exemplary approach may be advantageous in cases where, for instance, the growth is particularly dense or difficult to damage and/or destroy. In certain example embodiments, one or more sub-portions of the growth may be targeted, which may be particularly advantageous in cases where a growth is precariously positioned and/or otherwise difficult to attack.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of treating a patient having a growth, the method comprising:
   determining characteristics of the growth via an imaging system;
   generating a hologram corresponding to the growth using the determined characteristics;
   projecting a holographic image on the growth, the holographic image being projected in connection with a substantially coherent electromagnetic wave source;
   injecting magnetic particles into the patient; and
   causing the magnetic particles to migrate towards the projected holographic image so as to become attached to and/or embedded in the growth.

2. The method of claim 1, wherein the characteristics of the growth include the size, shape, and/or placement of the growth.

3. The method of claim 2, wherein the imaging system comprises CT, CAT, and/or MRI systems.

4. The method of claim 2, wherein the particles have a size of less than about 10 microns.

5. The method of claim 4, wherein the particles have a size of about 3-7 microns.

6. The method of claim 1, further comprising irradiating the particles with an energy source so as to at least partially damage and/or destroy the growth.

7. The method of claim 1, further comprising irradiating the particles with microwaves to damage and/or destroy the growth.

8. The method of claim 1, further comprising repeating said projecting and said causing for at least two portions of the growth.

9. The method of claim 6, further comprising further comprising repeating said projecting, said causing, and said irradiating for at least two portions of the growth.

10. The method of claim 2, further comprising:
    repeating said determining via the imaging system for the growth after the growth has been at least partially damaged to determine characteristics of the at least partially damaged growth;
    re-projecting a holographic image on the at least partially damaged growth; and
    causing the magnetic particles to migrate towards the projected holographic image so as to become attached to and/or embedded in the at least partially damaged growth.

11. The method of claim 10, further comprising repeating the steps of claim 10 until the growth is destroyed.

12. The method of claim 1, wherein the magnetic particles are coated in Teflon.

13. A system for treating a patient having a growth, comprising:
    an imaging system configured to determine characteristics of the growth;
    a controller configured to generate a hologram corresponding to the growth, the hologram being generated in dependence on said determined characteristics; and
    a holographic projection system configured to project a holographic image on the growth, the holographic image being projected in connection with a substantially coherent electromagnetic wave source;
    wherein the holographic projection system is further configured to generate a magnetic field in and/or on the growth such that magnetic particles injected into the patient will become attached to and/or embedded in the growth.

14. The system of claim 13, wherein the characteristics of the growth include the size, shape, and/or placement of the growth.

15. The system of claim 14, wherein the imaging system comprises CT, CAT, and/or MRI systems.

16. The system of claim 14, further comprising an irradiation system configured to irradiate the growth.

17. The system of claim 16, wherein the irradiation system is configured to irradiate the growth with microwaves.

18. The system of claim 14, further comprising a display configured to display data gathered by the imaging system.

19. A method of treating a patient having a growth, the method comprising:
    determining characteristics of the growth via an imaging system;
    generating a hologram corresponding to the growth using the determined characteristics;
    projecting a holographic image on the growth, the holographic image being projected in connection with a substantially coherent electromagnetic wave source;
    injecting particles into the patient;
    causing the particles to migrate towards the projected holographic image so as to become attached to and/or embedded in the growth; and
    irradiating the particles with microwaves so as to at least partially damage and/or destroy the growth;
    wherein the characteristics of the growth include the size, shape, and/or placement of the growth.

20. The method of claim 19, further comprising:
    repeating said determining via the imaging system for the growth after the growth has been at least partially damaged to determine characteristics of the at least partially damaged growth;
    re-projecting a holographic image on the at least partially damaged growth;
    causing the particles to migrate towards the projected holographic image so as to become attached to and/or embedded in the at least partially damaged growth; and
    irradiating the particles with microwaves so as to further damage and/or destroy the growth.

* * * * *